(12) United States Patent
Yuan et al.

(10) Patent No.: US 8,476,272 B2
(45) Date of Patent: *Jul. 2, 2013

(54) PHARMACEUTICAL COMPOSITION FOR TREATMENT OF TYPE 2 DIABETES

(75) Inventors: Kaihong Yuan, Lianyungang (CN); Piaoyang Sun, Lianyungang (CN)

(73) Assignee: Jiangsu Hengrui Medicine Co., Ltd., Lianyungang (CN)

( * ) Notice: Subject to any disclaimer, the term of this patent is extended or adjusted under 35 U.S.C. 154(b) by 103 days.

This patent is subject to a terminal disclaimer.

(21) Appl. No.: 13/257,945

(22) PCT Filed: Mar. 8, 2010

(86) PCT No.: PCT/CN2010/070910
§ 371 (c)(1),
(2), (4) Date: Sep. 20, 2011

(87) PCT Pub. No.: WO2010/111905
PCT Pub. Date: Oct. 7, 2010

(65) Prior Publication Data
US 2012/0010211 A1   Jan. 12, 2012

(51) Int. Cl.
*A61K 31/4985* (2006.01)
*A61P 3/10* (2006.01)
(52) U.S. Cl.
USPC .......................................................... 514/249
(58) Field of Classification Search
None
See application file for complete search history.

(56) References Cited

U.S. PATENT DOCUMENTS

2009/0105265 A1 * 4/2009 Kamali et al. ................ 514/249
2009/0124626 A1   5/2009 Kanda et al.

FOREIGN PATENT DOCUMENTS

| CN | 1391890 A | | 1/2003 |
| CN | 1478770 A | | 3/2004 |
| CN | 101277719 A | | 10/2008 |
| WO | WO 03/004498 | * | 1/2003 |
| WO | WO 2004/058266 | * | 7/2004 |

OTHER PUBLICATIONS

Amori et al. in JAMA 2007; 298(2):194-206.*
White et al. in Clinical Diabetes 26(2), 2008, 53-57.*
Demuth, H-U. et al., "Type 2 diabetes-Therapy with dipeptidyl peptidase IV inhibitors", Biochimica et Biophysica Acta 1751, pp. 33-44, 2005.
Augustyns, K. et al., "Inhibitors of proline-specific dipeptidyl peptidases: DPP IV Inhibitors as a novel approach for the treatment of Type 2 diabetes", Expert Opin. Ther. Patents, vol. 15, No. 10, pp. 1387-1407, 2005.

* cited by examiner

*Primary Examiner* — Dennis Heyer
(74) *Attorney, Agent, or Firm* — Birch, Stewart, Kolasch & Birch, LLP

(57) ABSTRACT

The present invention provides a pharmaceutical composition for the treatment of 2 type diabetes, wherein the pharmaceutical composition contains (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or its pharmaceutically acceptable salts and metformin or its pharmaceutically acceptable salts (such as hydrochlorate), preparation method thereof and method of treating 2 type diabetes with the composition.

22 Claims, No Drawings

PHARMACEUTICAL COMPOSITION FOR TREATMENT OF TYPE 2 DIABETES

This application is the national stage of International Application No. PCT/CN2010/070910 filed on Mar. 8, 2010.

FIELD OF THE INVENTION

The present invention relates to a pharmaceutical composition for the treatment of Type 2 diabetes, particularly relates to a pharmaceutical composition comprising fixed dose combinations of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or its salt and metformin or its salt (such as hydrochloride salt). The present invention also relates to the method for the preparation of the composition and for use of the composition for the treatment of Type 2 diabetes.

BACKGROUND OF THE INVENTION

Type 2 diabetes is a chronic and progressive disease arising from a complex pathophysiology involving the dual endocrine defects of insulin resistance and impaired insulin secretion. The treatment of Type 2 diabetes typically begins with diet and exercise, followed by oral antidiabetic monotherapy. For many patients, these regimens do not sufficiently control glycaemia during long term treatment, leading to a requirement of combination therapy within several years following diagnosis. However, co-prescription of two or more oral antidiabetic drugs may result in treatment regimens that are complex and difficult for many patients to follow. Combining two or more antidiabetic agents into a single tablet provides a potential means of delivering combination therapy without adding to the complexity of patients' daily regimens. Such formulations have been well accepted in other disease indications, such as hypertension (HYZAAR™ which is a combination of losartan potassium and hydrochlorothiazide) and cholesterol lowering (VYTORIN™ which is a combination of simvastatin and ezetimibe). The selection of effective and well-tolerated treatments is a key step in the design of a combination tablet. Moreover, it is essential that the components have complementary mechanism and compatible pharmacokinetic profiles. Examples of marketed combination tablets containing two oral antidiabetic agents include Glucovance™ (metformin and glyburide), Avandament™ (metformin and rosiglitazone), and Metaglip™ (metformin and glipizide).

Metformin represents the only oral antidiabetic agent proven to reduce the total burden of microvascular and macrovascular diabetic complications and to prolong the lives of Type 2 diabetes patients. Furthermore, metformin treatment is usually associated with the weight loss in overweight patients and with improvements in lipid profiles in dyslipidemic patients.

Dipeptidyl peptidase-4 (DPP-4) inhibitors represent a novel class of agents that are being developed for the treatment or improvement in glycemic control in patients with Type 2 diabetes. Specific drugs currently in clinical trials for the treatment of Type 2 diabetes include MK-0431, vildagliptin (LAF-237), saxagliptin (BMS-47718), P93/01 (Prosidon), SYR322 (Takeda), GSK823093, Roche0730699, TS021 (Taisho), E3024 (Eisai) and PHX-1149(Phenomix). For example, oral administration of vildagliptin to human Type 2 diabetes patients has been found to reduce fasting glucose and postprandial glucose excursion in association with significantly reduced HbAIC levels. For reviews on the application of DPP-4 inhibitors for the treatment of Type 2 diabetes, reference is made to the following publications: (1) H.-U. Demuth. et al. "Type 2 diabetes-Theraphy with dipeptidyl peptidase IV inhibitors", Biochim. Biophvs. Acta. 1751:33-44 (2005) and (2) K. Augustyns. et al. "Inhibitors of proline-specific dipeptidyl peptidases: DPP4 inhibitors as a novel approach for the treatment of Type 2 diabetes", Expert Opin. Ther. Patants, 15: 1387-1407 (2005).

SUMMARY OF THE INVENTION (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester having the following structural formula is compound A.

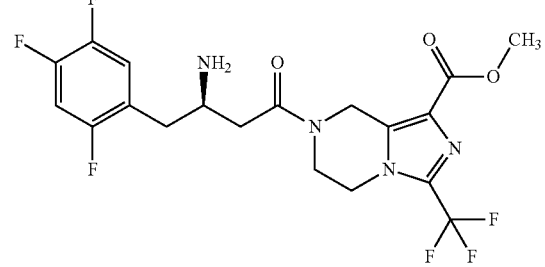

Compound A

The present invention provides a pharmaceutical composition of a fixed-dose combination of compound A or its salt and metformin which are prepared by dry or wet processing methods. The pharmaceutical composition of the present invention provides immediate release of the two active ingredients compound A or its salt and metformin, and immediate release of compound A or its salt together with slow release of metformin. In one embodiment, the pharmaceutical composition of the present invention is in form of a tablet, and in particular, a film-coated tablet. It can also be in other oral dosage forms such as a capsule.

The present invention also provides a method for the preparation of the pharmaceutical compositions of a fixed-dose combination of compound A or its salt and metformin by dry or wet processing methods. The dry processing methods include dry compression and dry granulation, and the wet processing methods include wet granulations.

Another aspect of the present invention provides a method for the treatment of Type 2 diabetes by administering to the patient in need of such treatment therapeutically effective amount of the pharmaceutical composition of the present invention.

These and other aspects will become readily apparent from the detailed description which follows.

The present invention relates to a novel pharmaceutical composition comprising a fixed-dose combination of compound A or its pharmaceutically acceptable salt and metformin or its pharmaceutically acceptable salt, method for the preparation of such pharmaceutical composition, and method for the treatment of Type 2 diabetes with such pharmaceutical composition. In particular, the present invention relates to the pharmaceutical composition comprising a fixed-dose combination of compound A or its pharmaceutically acceptable salt and metformin hydrochloride.

The inhibition time of compound A or its salt on the activity of DDP-4 is longer than that of MK-0431, and the inhibition intensity is stronger than that of MK-0431. Therefore, the composition comprising compound A or its salt and metformin or its salt is of great significance in clinical practice.

DETAILED DESCRIPTION OF THE INVENTION

In one aspect, the present invention relates to dosage form for the medicinal administration of a fixed-dose combination of compound A or its pharmaceutically acceptable salt and metformin or its pharmaceutically acceptable salt. Such dosage form may be in powder or solid form and includes tablet, capsule, sachet, etc. A specific solid dosage form relates to tablets comprising a fixed-dose combination of compound A or its pharmaceutically acceptable salt and metformin hydrochloride (1, 1-dimethylbiguanide hydrochloride).

The inhibition time of compound A or its salt on the activity of DDP-4 is longer than that of MK-0431, and the inhibition intensity is stronger than that of MK-0431. Therefore, the composition comprising compound A or its salt and metformin or its salt (such as hydrochloride salt) is of great significance in clinical practice.

In a specific aspect of the present invention, the composition comprises (1) compound A or its pharmaceutically acceptable salt, as one of the two active pharmaceutical ingredients; (2) metformin or its salt such as hydrochloride, as the second active pharmaceutical ingredient; and (3) lubricant or glidant. In an embodiment of this aspect of the present invention, the pharmaceutical composition may also contain one or more excipients which are selected from the group consisting of one or more binding agents (binders); one or more diluents; one or more surfactants or wetting agents; one or more disintegrants; and one or more antioxidants.

The pharmaceutically acceptable salts of compound A include but not limited to phosphate salt, hydrochloride salt, sulphate salt, nitrate salt, hydrobromide salt, mesylate salt, maleate salt, tartrate salt, succinate salt, acetate salt, trifluoroacetate salt, fumarate salt, citrate salt, benzene sulfonate salt, benzoate salt, naphthalenesulfonate salt, lactate salt, malate salt.

The dosage concentration of compound A or its salt incorporated into the pharmaceutical composition of the present invention is an amount from about 1 mg to about 500 mg of the activity moiety. A preferred dosage concentration of the compound A or its salt is an amount from about 25 mg to about 250 mg of the activity moiety. Discrete dosage concentrations are the equivalent of 25, 50, 75, 100, 150, 200, 300, 400 and 500 mg of compound A or its salt activity moiety.

The unit dosage concentration of compound A or the activity moiety of its salt incorporated into the fixed-dose combination pharmaceutical composition of the present invention is 25, 50, 75, 100, 150, 200, 300, 400 and 500 mg. A preferred dosage concentration of compound A or its salt is 50 or 100 mg.

The unit dosage concentration of the metformin hydrochloride incorporated into the fixed-dose combination of the present invention is 250, 500, 625, 750, 850, 1000, and 1500 mg. These unit dosage concentration of metformin hydrochloride represents the dosage concentration approved in China and for in U.S. for marketing to treat Type 2 diabetes.

The specific embodiments of dosage concentration of compound A or its salt and metformin or its salt such as hydrochloride salt in the fixed-dose combinations of the present invention are as following:

(1) 25 mg of compound A or its salt (e.g. 30.25 mg of phosphate salt) and 250 mg of metformin hydrochloride;
(2) 25 mg of compound A or its salt (e.g. 30.25 mg of phosphate salt) and 500 mg of metformin hydrochloride;
(3) 50 mg of compound A or its salt (e.g. 60.5 mg of phosphate salt) and 250 mg of metformin hydrochloride;
(4) 50 mg of compound A or its salt (e.g. 60.5 mg of phosphate salt) and 500 mg of metformin hydrochloride;
(5) 50 mg of compound A or its salt (e.g. 60.5 mg of phosphate salt) and 850 mg of metformin hydrochloride;
(6) 50 mg of compound A or its salt (e.g. 60.5 mg of phosphate salt) and 1000 mg of metformin hydrochloride;
(7) 100 mg of compound A or its salt (e.g. 121.0 mg of phosphate salt) and 250 mg of metformin hydrochloride;
(8) 100 mg of compound A or its salt (e.g. 121.0 mg of phosphate salt) and 500 mg of metformin hydrochloride;
(9) 100 mg of compound A or its salt (e.g. 121.0 mg of phosphate salt) and 850 mg of metformin hydrochloride;
(10) 100 mg of compound A or its salt (e.g. 121.0 mg of phosphate salt) and 1000 mg of metformin hydrochloride;
(11) 100 mg of compound A or its salt (e.g. 121.0 mg of phosphate salt) and 1500 mg of metformin hydrochloride;

The pharmaceutical composition of the present invention are prepared by wet or dry processing methods. In one embodiment the pharmaceutical composition is prepared by wet processing methods. In a class of this embodiment the pharmaceutical composition is prepared by wet granulation methods. Either high-shear granulation or fluid-bed granulation can be used in the wet granulation. In one embodiment, employing fluid-bed granulation has the advantage of affording tablets with higher radial strength.

In a second embodiment the pharmaceutical composition is prepared by dry processing methods. In a class of this embodiment the pharmaceutical composition is prepared by direct compression or dry granulation methods. An embodiment of dry granulation is roller compaction.

The pharmaceutical composition obtained by the dry or wet processing methods may be compressed into tablets, encapsulated or metered into sachets.

The pharmaceutical composition contains one or more lubricants or glidants. Examples of lubricants include magnesium stearate, calcium stearate, stearic acid, sodium stearyl fumarate, hydrogenated castor oil, and mixture thereof. A preferred lubricant is magnesium stearate or sodium stearyl fumarate or mixture thereof. Examples of glidants include colloidal silicon dioxide, calcium phosphate, magnesium silicate, and talc.

The pharmaceutical composition of the present invention optionally contains one or more binding agents. Embodiments of binding agents include hydroxypropylcellulose (HPC), hydroxypropylmethyl cellulose (HMPC), hydroxyethyl cellulose, starch 1500, polyvinylpyrrolidone (povidone), and co-povidone. A preferred binding agent is polyviylpyrrolidone.

The pharmaceutical composition of the present invention may also optionally contain one or more diluents. Examples of diluents include mannitol, sorbitol, calcium dihydrophosphate dihydrate, microcrystalline cellulose, and powdered cellulose. A preferred diluent is microcrystalline cellulose. Microcrystalline cellulose is available from several suppliers including Avicel PH 101, Avicel PH 102, Avicel PH 103, Avicel PH 105, and Avicel PH 200, manufactured by FMC corporation.

The pharmaceutical composition of the present invention may also optionally contain a disintegrant. The disintegrant may be one of several modified starches, modified cellulose polymers, or polycarboxylic acids, such as crosslinking hydroxymethylcellulose sodium , starch sodium glycollate, polacrillin potassium, and hydroxymethylcellulose calcium (CMC Calcium). In one embodiment, the disintegrant is crosslinking hydroxymethylcellulose sodium. Crosslinking hydroxymethylcellulose sodium NF Type A is commercially available under the trade name "Ac-di-sol."

The pharmaceutical composition of the present invention may also optionally contain one or more surfactants or wetting agents. The surfactant may be anionic, cationic, or neutral. Anionic surfactants include sodium lauryl sulfate, sodium dodecanesulfonate, sodium oleyl sulfate, and sodium laurate mixed with stearates and talc. Cationic surfactants include benzalkonium chlorides and alkyltrimethylammonium bromides. Neutral surfactants include glyceryl monooleate, polyoxyethylene dehytrated sorbitan fatty acid ester, polyvinyl alcohol, and dehydrated sorbitan ester. Embodiments of wetting agents include poloxamer, polyoxyethylene alkyl ether, polyoxyethylene castor oil derivatives, and polyoxyethylene stearate.

An anti-oxidant may optionally be added to the formulation to impart chemical stability. The anti-oxidant is selected from the group consisting of $\alpha$-tocopherol, $\gamma$-tocopherol, $\delta$-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), and butylated hydroxyanisole (BHA). In one embodiment, the antioxidant is BHT or BHA.

Preferred dosage form for the pharmaceutical composition of the present invention is tablet which is prepared by compression methods. Such tablet may be film-coated with such as a mixture of hydroxypropylcellulose and hydroxypropylmethylcellulose. The mixture contains titanium dioxide and/or other coloring agents, such as iron oxide, dyes, and lakes; a mixture of polyvinyl alcohol (PVA) and polyethylene glycol (PEG) containing titanium dioxide and/or other coloring agents, such as iron oxide, dyes, and lakes; or any other suitable immediate-release film-coating agent(s). The coat provides taste masking and additional stability to the final tablet. A commercial film-coat is Opadry® which is a formulated powder blend provided by Colorcon.

Finally, a sweetening agent and/or flavoring agent may be added if desired.

In one embodiment of the present invention, the pharmaceutical composition contains about 3 to 20% by weight of compound A or its salt as one of the two pharmaceutically active ingredients; about 25 to 94% by weight of metformin or its salt (such as hydrochloride salt) as the second pharmaceutically active ingredient; about 0 to 35% by weight of a binding agent; and about 0.1 to 10% by weight of a lubricant. In a class of this embodiment the binding agent is polyvinylpyrrolidone or hydroxypropylcellulose, and the lubricant is magnesium stearate or sodium stearyl fumarate. In a subclass of this class, the binding agent is polyvinylpyrrolidone, and the lubricant is sodium stearyl fumarate. In another class the pharmaceutical composition optionally contains about 0 to is 3% by weight of a surfactant and/or about 0 to 70% by weight of a diluent. In a subclass of this class, the surfactant is sodium lauryl sulfate and the diluent is microcrystalline cellulose.

In a second embodiment the pharmaceutical composition of the present invention is prepared by wet granulation methods and contains about 5 to 18% by weight of compound A or its salt as one of the two pharmaceutically active ingredients; about 65 to 77% by weight of metformin or its salt (such as hydrochloride salt) as the second pharmaceutically active ingredient; about 4 to 9% by weight of a binding agent; and about 1 to 2% by weight of a lubricant. In a class of this embodiment the binding agent is polyvinylpyrrolidone or hydroxypropylcellulose, and the lubricant is magnesium stearate or sodium stearyl fumarate. In a subclass of this class, the binding agent is polyvinylpyrrolidone. In another class the pharmaceutical composition optionally contains about 0.5 to 1% by weight of a surfactant and/or about 5 to 15% by weight of a diluent. In a subclass of this class, the surfactant is sodium lauryl sulfate and the diluent is microcrystalline cellulose.

In a further embodiment of the present invention, the pharmaceutical composition envisioned for commercial development is as following:

Tablets of 50 mg of compound A or its salt/500 mg of metformin or its salt such as hydrochloride salt potency:
About 9% by weight of the compound A or its salt; about 73% by weight of metformin or its salt such as hydrochloride salt; about 7% by weight of the binding agent; about 1 to 2% by weight of the lubricant; and optionally about 10% by weight of the diluent and/or about 0.5% by weight of the surfactant. In a class of this embodiment the active ingredient is compound A or its salt, the binding agent is polyvinylpyrrolidone, the lubricant is magnesium stearate or sodium stearyl fumarate, the diluent is microcrystalline cellulose, and the surfactant is sodium lauryl sulfate.

Tablets of 50 mg of compound A or its salt/850 mg of metformin or its salt such as hydrochloride salt potency:
About 6% by weight of compound A or its salt; about 76% by weight of metformin or its salt such as hydrochloride salt; about 7% by weight of the binding agent; about 1 to 2% by weight of the lubricant; and optionally about 10% by weight of the diluent and/or about 0.5% by weight of the surfactant. In a class of the embodiment the lubricant is magnesium stearate or sodium stearyl fumarate, the diluent is microcrystalline cellulose, and the surfactant is sodium lauryl sulfate.

Tablets of 50 mg of compound A or its salt/1000 mg of metformin or its salt such as hydrochloride salt potency:
About 5% by weight of compound A or its salt; about 77% by weight of metformin hydrochloride; about 7% by weight of the binding agent; about 1 to 2% by weight of the lubricant; and optionally about 10% by weight of the diluent and/or about 0.5% by weight of the surfactant. In a class of this embodiment the active ingredient is compound A or its salt; the binding agent is polyvinylpyrrolidone, the lubricant is magnesium stearate or sodium stearyl fumarate, the diluent is microcrystalline cellulose, and the surfactant is sodium lauryl sulfate.

Tablets of 100 mg of compound A or its salt/500 mg of metformin or its salt such as hydrochloride salt potency:
About 17% by weight of compound A or its salt; about 65% by weight of metformin hydrochloride; about 7% by weight of the binding agent; about 1 to 2% by weight of the lubricant; and optionally about 9% by weight of the diluent and/or about 0.5% by weight of the surfactant. In a class of this embodiment the active ingredient is compound A or its salt; the binding agent is polyvinylpyrrolidone, the lubricant is magnesium stearate or sodium stearyl fumarate, the diluent is microcrystalline cellulose, and the surfactant is sodium lauryl sulfate.

Tablets of 100 mg of compound A or its salt/850 mg of metformin or its salt such as hydrochloride salt potency:
About 11% by weight of compound A or its salt; about 75% by weight of metformin hydrochloride; about 7% by weight of the binding agent; about 1 to 2% by weight of the lubricant; and optionally about 4% by weight of the diluent and/or about 0.5% by weight of the surfactant. In a class of this embodiment the active ingredient is compound A or its salt; the binding agent is polyvinylpyrrolidone, the lubricant is magnesium stearate or sodium stearyl fumarate, the diluent is microcrystalline cellulose, and the surfactant is sodium lauryl sulfate.

Tablets of 100 mg of compound A or its salt/1000 mg of metformin or its salt such as hydrochloride potency:

About 10% by weight of compound A or its salt; about 77% by weight of metformin hydrochloride; about 7% by weight of the binding agent; about 1 to 2% by weight of the lubricant; and optionally about 4% by weight of the diluent and/or about 0.5% by weight of the surfactant. In a class of this embodiment the active ingredient is compound A or its salt; the binding agent is polyvinylpyrrolidone, the lubricant is magnesium stearate or sodium stearyl fumarate, the diluent is microcrystalline cellulose, and the surfactant is sodium lauryl sulfate.

The metformin or its salt such as hydrochloride salt of the present invention may be immediate release or slow release.

The pharmaceutical tablet composition of the present invention may also contain one or more additional formulation ingredients selected from a wide variety of excipients known in the pharmaceutical formulation art. According to the desired properties of the pharmaceutical compositions, any kind of ingredients may be selected, alone or in combination, based upon their known uses in preparing tablet compositions. Such ingredients include, but are not limited to, diluents, compression aids, glidants, disintegrants, lubricants, flavors, flavor enhancers, sweeteners, and preservatives.

The term "tablet" as used herein is intended to compressed pharmaceutical dosage formulations of all shapes and sizes, whether coated or uncoated. Substances which may be used for coating include hydroxypropylcellulose, hydroxypropylmethylcellulose, titanium dioxide, talc, sweeteners, colorants, and flavor enhancers.

In one embodiment the pharmaceutical composition of the present invention is prepared by wet granulation (high shear and/or fluid bed). Granulation is a process in which binding agent is added either to the granulating solution or to the granulating bowl to form granules. The steps involved in the wet granulation method comprise the following:

(1) the active pharmaceutical ingredients metformin or its salt such as hydrochloride salt and compound A or its salt are added to the granulating bowl;
(2) the optional disintegrants are added to step 1;
(3) with regard to high shear granulation, the binding agent (such as polyvinylpyrrolidone or hydroxypropylcellulose) is dried and added to the granulating bowl and dry mixed for a short period followed by adding of water with or without surfactant (such as sodium lauryl sulfate). With regard to fluid bed granulation, both active pharmaceutical ingredients are added to the granulator bowl and the granulating solution consisted of binding agent aqueous solution is added upon fluidization with or without surfactant;
(4) granules prepared by high shear granulation are tray-dried in an oven or dried in a fluid bed dryer. For the granules prepared by fluid bed granulation, the granules are dried in a fluid bed dryer;
(5) dried granules are resized in a suitable grinder;
(6) the optional diluents (such as microcrystalline cellulose and calcium dihydrophosphate dihydrate) are blended with dried granules in a suitable blender;
(7) lubricants or glidants (such as magnesium stearate and sodium stearyl fumarate) are added to the blend from step 6 in a suitable blender;
(8) the lubricated granule mixture from step 7 may be filled into bottles, sachets, or capsules or compressed into desired tablet image;
(9) and if desired, the resulting tablets may be film-coated.

The steps involved in the dry processing (direct compression or dry granulation) methods comprise:

(1) the active pharmaceutical ingredients metofrmin hydrochloride and compound A or its slat are added to a suitable blender;
(2) the optional disintegrants are added to step 1;
(3) the optional binders and/or diluents are added to step 2;
(4) lubricants or glidants are added to step 3;
(5) mixture from step 4 may be filled into bottles, sachets, or capsules or compressed into desired tablet image, or processed through a roller compactor;
(6) if processed through a roller compaction, granules may be resized in a suitable mill, if necessary;
(7) the optional diluents may be added to the resulting granules, in a suitable blender to improve compaction properties;
(8) the optional lubricants or glidants are added to the blend from step 7;
(9) the lubricated granule mixture from step 8 may be filled into bottles, sachets, or capsules or compressed into desired tablet image;
(10) and if desired, the resulting tablets from step 5 or step 9 may be film-coated.

The present invention also provides methods for treatment of Type 2 diabetes by orally administering to a subject in need of such treatment a therapeutically effective amount of one of the fixed-dose combination pharmaceutical compositions of the present invention. In one embodiment the subject in need of such treatment is human. In another embodiment the pharmaceutical composition is in tablet form. The pharmaceutical composition comprising the fixed-dose combination may be administered once-daily (QD), twice-daily (BID), or thrice-daily (TID).

The following examples further describe and demonstrate the embodiments within the scope of the present invention. The examples are given only for the purpose of illustration and are not intended to be consider as limitations of the present invention as many variations thereof are possible without departing from the spirit and scope of the invention.

EXAMPLE 1

Fixed-dose Combination of 50 mg of Compound A and 500 mg of Metformin Hydrochloride/per Tablet-wet Granulation

| | |
|---|---|
| Compound A | 50 mg |
| Metformin hydrochloride | 500 mg |
| Polyvinlypyrrolidone | 48.2 mg |
| Sodium lauryl sulfate (SLS) | 3.45 mg |
| Microcrystalline cellulose (Avicel PH-102) | 59.3 mg |
| Sodium stearyl fumarate | 13.8 mg |
| Purified water for granulation step* | 39.8 mg for high shear or 354 mg for fluid bed |
| Opadry ® II | 17.2 mg |
| Purified water for coating step* | 68.9 mg |

*Removed during processing

Method of Manufacture:

Compound A and metformin hydrochloride were loaded into a high shear granulator or a fluid bed granulator. In the case of high shear granulation, in addition to the polyvinylpyrrolidone binding agent, the purified water containing sodium lauryl sulfate was added to the APIs (active pharmaceutical ingredients), over a period of 3-5 minutes. The wet substances were either tray-dried at 40° C. or dried in a fluid-bed dryer at an inlet temperature of 45-60° C. for 3-6 minutes. In the case of fluid bed granulation, the purified water containing polyvinylpyrrolidone and sodium lauryl sulfate was added to APIs over a period of 30-60 minutes. The wet substances were dried in a fluid-bed dryer at an inlet temperature of 45-60° C. The dried material was then milled using a co-mill to achieve fine granules. After milling, the microcrystalline cellulose was added to the granules and blended in a twin shell-blender for 200 revolutions. The lubricant (sodium stearyl fumarate) was then added and blended an additional 100 revolutions. The lubricated mixture was compressed using a rotary tablet press to provide 675 mg of uncoated tablet. The tablets were optionally coated with Opadrytm II suspension (polyvinyl alcohol, polyethylene glycol, titanium dioxide, and talc, with or without colorants) to an approximate 2.5% weight gain to provide 692 mg of coated tablet.

Specific description: 50 mg of compound A in the formulation may be the pharmaceutically acceptable salt of compound A as well, such as 60.5 mg of phosphate of compound A, by inference, examples 2-7 hereinafter are in the same way, and they won't be repeated. Metformin hydrochloride may be metformin or other pharmaceutically acceptable salt as well. Examples 2-7 hereinafter are in the same way, and they won't be repeated again.

EXAMPLE 2

Fixed-dose Combination of 50 mg of Compound A and 850 mg of Metformin Hydrochloride/per Tablet-wet Granulation

| | |
|---|---|
| Compound A | 50 mg |
| Metformin hydrochloride | 850 mg |
| Polyvinlypyrrolidone | 78.2 mg |
| Sodium lauryl sulfate (SLS) | 5.60 mg |
| Microcrystalline cellulose (Avicel PH-102) | 96.1 mg |
| Sodium stearyl fumarate | 22.3 mg |
| Purified water for granulation step* | 64.9 mg for high shear or 573 mg for fluid bed |
| Opadry ® II | 27.9 mg |
| Purified water for coating step* | 112 mg |

*Removed during processing

Method of Manufacture:

Tablets were prepared by wet-granulation using essentially the procedure of Example 1 to provide 1103 mg uncoated tablet. The tablets were optionally coated with 27.9 mg of standard Opadry® II film-coated preparations to provide 1131 mg of coated tablet.

EXAMPLE 3

Fixed-dose Combination of 50 mg of Compound A and 1000 mg of Metformin Hydrochloride/per Tablet-wet Granulation

| | |
|---|---|
| Compound A | 50 mg |
| Metformin hydrochloride | 1000 mg |
| Polyvinlypyrrolidone | 91.0 mg |
| Sodium lauryl sulfate (SLS) | 6.50 mg |
| Microcrystalline cellulose (Avicel PH-102) | 112.3 mg |
| Sodium stearyl fumarate | 26 mg |
| Purified water for granulation step* | 75.5 mg for high shear or 667 mg for fluid bed |
| Opadry ® II | 32.5 mg |
| Purified water for coating step* | 130 mg |

*Removed during processing

Method of Manufacture:

Tablets were prepared by wet-granulation using essentially the procedure of Example 1 to provide 1286 mg uncoated tablet. The tablets obtained were optionally coated with an Opadry® II suspension (polyvinyl alcohol, polyethylene glycol, titanium dioxide, and talc, with or without colorants) to an approximate 2.5% weight gain to provide 1319 mg of coated tablet.

EXAMPLE 4

Fixed-dose Combination of 50 mg of Compound A and 500 mg of Metformin Hydrochloride/per Tablet-wet Granulation

| | |
|---|---|
| Compound A | 50 mg |
| Metformin hydrochloride | 500 mg |
| Polyvinlypyrrolidone | 48.2 mg |
| Microcrystalline cellulose (Avicel PH-102) | 69.6 mg |
| Magnesium stearate | 6.89 |
| Purified water for granulation step* | 39.8 mg for high shear or 354 mg for fluid bed |
| Opadry ® II | 17.2 mg |
| Purified water for coating step* | 68.9 mg |

*Removed during processing

Method of Manufacture:

Compound A and metformin hydrochloride were loaded into a high shear granulator or a fluid bed granulator. In the case of high shear granulation, n addition to the polyvinylpyrrolidone binding agent, purified water was added to the APIs over a period of 3-5 minutes. The wet substances were either tray-dried at 40° C. or dried in a fluid-bed dryer at an inlet temperature of 45-60° C. for 3-6 minutes. In the case of fluid bed granulation, purified water containing polyvinylpyrrolidone and sodium lauryl sulfate was added to APIs over a period of 30-60 minutes. The wet substances were dried in a fluid-bed dryer at an inlet temperature of 45-60° C. The dried material was then milled using a co-mill to achieve fine granules. After milling, microcrystalline cellulose was added to the granules and blended in a twin shell-blender for 200 revolutions. The lubricant (magnesium stearate) was then added and blended an additional 100 revolutions. The lubricated mixture was compressed using a rotary tablet press to provide 675 mg uncoated tablet. The tablet was then optionally film-coated with Opadry® II suspension (polyvinyl alcohol, polyethylene glycol, titanium dioxide, and talc, with or without colorants) to an approximate 2.5% weight gain to provide 692 mg of coated tablet.

EXAMPLE 5

Fixed-dose Combination of 50 mg of Compound A and 1000 mg of Metformin Hydrochloride/per Tablet-wet Granulation

| | |
|---|---|
| Compound A | 50 mg |
| Metformin hydrochloride | 1000 mg |
| Polyvinlypyrrolidone | 91.0 mg |
| Microcrystalline cellulose (Avicel PH-102) | 125.25 mg |
| Magnesium stearate | 13.0 |
| Sodium lauryl sulfate | 6.5 |
| Purified water for granulation step* | 75.5 mg for high shear or 667 mg for fluid bed |
| Opadry ® II | 32.5 mg |
| Purified water for coating step* | 130 mg |

*Removed during processing

Method of Manufacture:

Compound A and metformin hydrochloride were loaded into a high shear granulator or a fluid bed granulator. In the case of high shear granulation, in addition to the polyvinylpyrrolidone binding agent, purified water containing sodium lauryl sulfate was added to the APIs, over a period of 3-5 minutes. The wet substances were either tray-dried at 40° or dried in a fluid-bed dryer at an inlet temperature of 45-60° for 3-6 minutes. In the case of fluid bed granulation, purified water containing polyvinylpyrrolidone was added to APIs over a period of 30-60 minutes. The wet substances were dried in a fluid-bed dryer at an inlet temperature of 45-60° C. The dried material was then milled using a co-mill to achieve fine granules. After milling, microcrystalline cellulose was added to the granules and blended in a twin shell-blender for 200 revolutions. The lubricant (magnesium stearate) was then added and blended an additional 100 revolutions. The lubricated mixture was compressed using a rotary tablet press to provide 1286 mg uncoated tablet. The tablet was then optionally film-coated with Opadry® II suspension (polyvinyl alcohol, polyethylene glycol, titanium dioxide, and talc, with or without colorants) to an approximate 2.5% weight gain to provide 1319 mg of coated tablet.

EXAMPLE 6

Fixed-dose Combination of 100 mg of Compound A and 1000 mg of Metformin Hydrochloride/per Tablet-wet Granulation

| | |
|---|---|
| Compound A | 100 mg |
| Metformin hydrochloride | 1000 mg |
| Polyvinlypyrrolidone | 91.0 mg |
| Sodium lauryl sulfate (SLS) | 6.50 mg |
| Microcrystalline cellulose (Avicel PH-102) | 48 mg |
| Sodium stearyl fumarate | 26 mg |
| Purified water* | 667 mg |

*Removed during processing

Method of Manufacture:

Tablets were prepared by fluid-bed granulation using essentially the procedure of Example 1 to provide 1271.50 mg of uncoated tablet.

EXAMPLE 7

Fixed-dose Combination of 100 mg of Compound A and 500 mg of Metformin Hydrochloride/per Tablet-wet Granulation

| | |
|---|---|
| Compound A | 100 mg |
| Metformin hydrochloride | 500 mg |
| Polyvinlypyrrolidone | 53.8 mg |
| Sodium lauryl sulfate (SLS) | 3.84 mg |
| Microcrystalline cellulose (Avicel PH-102) | 66.5 mg |
| Sodium stearyl fumarate | 15.4 mg |
| Purified water* | 394 mg |

*Removed during processing

Method of Manufacture:

Tablets were prepared by fluid-bed granulation using essentially the procedure of Example 1 to provide 739.50 mg of uncoated tablet.

Test 1: In vitro Activity and Selectivity Study of Compound A and MK-0431

Method:

Thawed DPP4-Glo. was buffered and balanced to room temperature, and cryopreserved fluorescein test agent was buffered before use. DPP4-Glo.

was suspended in substrate and ultrapure water was added, the mixture was mixed slightly to uniformity to provide 1 mM of substrate. The fluorescein test agent was put into amber bottle, and DPP4-Glo. was added. The fluorescein test agent should be dissolved in 1 min. The test compound was dissolved with DMSO to 50 times of the final processing concentration. 2 μL of test compound of 50 times concentration was added into each test tube, and 2 μL of DMSO was added into negative control and blank control. 46 μL of Tris buffer solution was added into each test tube , and 48 μL of Tris buffer solution was added into blank control. 2 μL of DPP4 enzyme was added into each test tube of negative control and test sample, and the test tubes were shaken and mixed, and then centrifuged. The substances in the test tubes were all transferred to a 96-well plate, and the substrates and DPP4-Glo. were mixed in a proportion of 1:49. The mixture was shaken and mixed adequately. 50 μL of the mixture of DDP4-Glo. and the substrate was added into each 96-well plate well after standing for 30-60 minutes at room temperature, the plate was sealed with film. The substances in the 96 wells were mixed slowly with plate scillator at 300-500 rmp/30 s. After cultivation for 30 minutes to 3 hours at room temperature, the chemiluminescence value was measured with NOVOstar multifunction microplate reader.

TABLE 1

|  | DPP4 $IC_{50}(M)$ | DPP8 | | DPP9 | |
|---|---|---|---|---|---|
| Test compound | | $IC_{50}(M)$ | selectivity ratio (DPP8/DPP4) | $IC_{50}(M)$ | selectivity ratio (DPP9/DPP4) |
| Compound A | 0.008 | 26.1 | 3263 | 75.5 | 9438 |
| MK-0431 | 0.019 | 25.8 | 1358 | 92.7 | 4879 |

Result: The inhibition activity of compound A on DDP4 is better than the control drug MK-O431 as well as the inhibition selectivity.

Test 2: The Inhibition of Compound A and MK-0431 on the DPP4 Activity of Macaca Fascicularis Serum by Single Administration Respectively The experimental animals were 8 healthy adult macaca fascicularis, half male and half female. The macaca fascicularis was orally administered with the testing compounds after fasting more than 8 hours while water intake freely. Venous blood was collected before administration or 1, 3, 9, 12 and 24 hours after administration respectively. The serum was separated after centrifuged at 3000 rpm for 10 minutes. The activity of DPP4 was determined, and the inhibition and duration time of the serum DPP4 activity after single administration of 10 mg/kg of compound A or MK-0431 to macaca fascicularis were observed. The concentrations of compound A or MK-0431 in serum were determined with liquid chromatography-tandem mass spectrometry. Crossover administration was applied in the experiment, the animals could be administered one more time only after a rest for at least 7-10 days from last administration.

TABLE 2

The effect of 10 mg/kg of compound A or MK-O431 by oral administration on the DPP4 activity of *macaca fascicularis* (DPP4 specific activity %)

| | Administration time (h) | | | | | |
|---|---|---|---|---|---|---|
| | 0 | 1 | 3 | 9 | 12 | 24 |
| Compound A | 100.0 | 23.5 ± 6.5 | 3.8 ± 0.6 | 9.1 ± 1.6 | 22.0 ± 3.1 | 40.9 ± 4.0 |
| MK-0431 | 100.0 | 35.7 ± 9.8 | 12.2 ± 1.0 | 39.0 ± 3.0 | 48.9 ± 3.6 | 62.5 ± 2.0 |

Table 2 indicates that compound A inhibits serum DPP4 activity of macaca fascicularis significantly after single oral administration. The inhibition intensity and duration time are both better than that of MK-0431 at the same dosage. 10 mg/kg of compound A can keep the serum DPP4 activity inhibitor at more than 75% in 12 hours.

Test 3: The Effect of Compound A and MK-0431 in Combination with Metformin Respectively on Genetic Fatty Wistar Rats with Diabetes 14-19 week-old male Wistar rats were divided into 5 groups, 5-6 each group. Compound A (10mg/kg body weight/day, p.o.), MK-0431 (10 mg/kg body weight/day, p.o.), metformin (100 mg/kg body weight/day; mixed in commercial feed in the ratio of 5ppm) are administered to the Wistar rats for 14 days. Blood was collected from caudal vein. The plasma glucose and hemoglobin Al were determined respectively with a commercial kit (NC-ROPET, Nippon Chemiphar CO.) by enzyme method. Results were expressed as mean value of each group (n=5-6)±standard deviation by Dunnett's test analysis which were shown in table 3. A significance level of 1% was used.

TABLE 3

| | plasma glucose | hemoglobin |
|---|---|---|
| control group | 346 ± 30 | 5.8 ± 0.4 |
| compound A | 214 ± 50* | 5.3 ± 0.3 |
| metformin | 327 ± 46 | 6.1 ± 0.6 |
| MK-0431 + metformin | 185 ± 13* | 4.8 ± 0.5* |
| Compound A + metformin | 154 ± 23* | 4.2 ± 0.4* |

*P < 0.01 compared with control group

In table 3 the administration of compound A in combination with metformin significantly decreases the concentrations of plasma glucose and hemoglobin, and the intensity is greater than administration of MK-0431 in combination with metformin.

Test 4: Glucosieloading Study of Phosphate of Compound A, Phosphate of MK-0431 in Combination with Metformin Respectively on Genetic Fatty Wistar Rats with Diabetes 13-14 week-old male Wistar rats were divided into 5 groups, 5 each group. Phosphate of compound A (30 mg/kg body weight/day, p.o.), phosphate of MK-0431 (30mg/kg body weight/day, p.o.), metformin (100 mg/kg body weight/day) are administered to the Wistar rats for 7 days. Oral glucosieloading test was conducted immediately after fasting overnight (2 g glucose/kg/5 ml, p.o.). Blood was collected from caudal vein before or 120 minutes and 240 minutes after the test, and plasma glucose was analyzed with enzyme method (Encore Chemical System; Baker). Results were expressed as the mean value of each group (n=5)±SD by Dunnett's test analysis which were shown in table 4.

TABLE 4

| | plasma glucose (mg/dl) | | |
|---|---|---|---|
| Group | 0 min | 120 min | 240 min |
| control | 120 ± 8 | 242 ± 57 | 138 ± 19 |
| phosphate of compound A | 103 ± 11 | 137 ± 17* | 102 ± 9* |
| metformin | 119 ± 11 | 221 ± 62 | 107 ± 21* |
| phosphate of MK-0431 + metformin | 109 ± 5 | 116 ± 7* | 86 ± 3* |
| phosphate of compound A + metformin | 107 ± 3 | 95 ± 10* | 64 ± 5* |

*compared with control group P < 0.01

Table 4 shows clearly that the administration of phosphate of compound A in combination with metformin significantly inhibit the increase of plasma glucose after glucosieloading test, and the intensity is greater than administration of MK-0431 in combination with metformin.

What is claimed is:

1. A pharmaceutical composition comprising:
   (a) about 3 to 20% by weight of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof;
   (b) about 25 to 94% by weight of metformin or a salt thereof;
   (c) about 0.1 to 10% by weight of lubricant; and
   (d) about 0 to 35% by weight of binding agent.

2. The pharmaceutical composition as claimed in claim 1 additionally comprising one or more excipients selected from the group consisting of (a) diluent, (b) disintegrant, (c) surfactant, (d) wetting agent, and (e) anti-oxidant.

3. The pharmaceutical composition as claimed in claim 1 comprising:
   (a) about 5 to 18% by weight of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof;
   (b) about 65 to 77% by weight of metformin or the salt thereof;
   (c) about 1 to 2% by weight of lubricant; and
   (d) about 4 to 9% by weight of binding agent.

4. The pharmaceutical composition as claimed in claim 3 additionally comprising about 0.5 to 1% by weight of surfactant and/or about 5 to 15% by weight of diluent.

5. The pharmaceutical composition as claimed in claim 3, wherein the lubricant is magnesium stearate or sodium stearyl fumarate, and the binding agent is polyvinylpyrrolidone.

6. The pharmaceutical composition as claimed in claim 3 comprising:
   (a) about 9% by weight of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof;
   (b) about 73% by weight of metformin or the salt thereof;
   (c) about 1 to 2% by weight of lubricant; and
   (d) about 7% by weight of binding agent.

7. The pharmaceutical composition as claimed in claim 6 additionally comprising about 0.5% by weight of surfactant and/or about 10% by weight of diluent.

8. The pharmaceutical composition as claimed in claim 3 comprising:
   (a) about 5% by weight of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof;
   (b) about 77% by weight of metformin or the salt thereof;
   (c) about 1 to 2% by weight of lubricant; and
   (d) about 7% by weight of binding agent.

9. The pharmaceutical composition as claimed in claim 8 additionally comprising about 0.5% by weight of surfactant and/or about 10% by weight of diluent.

10. A pharmaceutical composition comprising:
    (a) (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or a pharmaceutically acceptable salt thereof as a unit dosage of 25 to 500 mg;
    (b) metformin or a salt thereof as a unit dosage of 250, 500, 625, 750, 850, 1000, 1250 or 1500 mg;
    (c) about 1 to 2% by weight of lubricant;
    (d) about 7% by weight of binding agent; optionally
    (e) about 10% by weight of diluent; and optionally
    (f) about 0.5% by weight of surfactant.

11. The pharmaceutical composition as claimed in claim 10, wherein the lubricant is sodium stearyl fumarate; the binding agent is polyvinylpyrrolidone; the optional diluent is microcrystalline cellulose, and the optional surfactant is sodium lauryl sulfate.

12. The pharmaceutical composition as claimed in claim 10, wherein the (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof is present as a unit dosage of 25, 50, 75, 100, 150, 200, 300, 400 or 500 mg, and the metformin or its salt is present as a unit dosage of 250, 500, 850, 1000, 1250 or 1500 mg.

13. The pharmaceutical composition as claimed in claim 12, wherein the (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof is present as a unit dosage of 50 or 100 mg, and the metformin or its salt is present as a unit dosage of 500, 850 or 1000 mg.

14. The pharmaceutical composition as claimed in claim 1 or claim 12, wherein the pharmaceutical composition is in the form of a tablet or other oral dosage form.

15. A method for the treatment of Type 2 diabetes in a human in need thereof, which comprises oral administration of the pharmaceutical composition as claimed in claim 1 or 12.

16. The pharmaceutical composition as claimed in claim 1 or claim 12, which further comprises one or more agents selected from the group consisting of flavoring agents, colorants, and sweeteners.

17. The pharmaceutical composition as claimed in claim 1 or claim 12 prepared by wet granulation methods.

18. The pharmaceutical composition as claimed in claim 1 or claim 12, wherein the pharmaceutically acceptable salt is selected from the group consisting of phosphate salt, hydrochloride salt, sulphate salt, nitrate salt, hydrobromide salt, mesylate salt, maleate salt, tartrate salt, succinate salt, acetate salt, trifluoroacetate salt, fumarate salt, citrate salt, benzene sulfonate salt, benzoate salt, naphthalenesulfonate salt, lactate salt or malate salt.

19. The method according to claim 15, wherein the administered daily dose of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester or the pharmaceutically acceptable salt thereof is 25 mg to 1000 mg, and the administered daily dose of metformin or its salt is 250 mg to 3000 mg.

20. The method according to claim 15, wherein the pharmaceutical composition is administered once daily, twice daily or thrice a day.

21. The pharmaceutical composition as claimed in any one of claims 1, 3, 6, 8, 10, 12, and 13, wherein the metformin is in the form of the hydrochloride salt.

22. The method according to claim 15, wherein the metformin is in the form of the hydrochloride salt.

* * * * *